US009585198B2

United States Patent
Modrzejewski et al.

(10) Patent No.: US 9,585,198 B2
(45) Date of Patent: Feb. 28, 2017

(54) VARIABLE STIFFNESS BLANKET WITH VARIABLE HEATING

(71) Applicant: BELL HELICOPTER TEXTRON INC., Fort Worth, TX (US)

(72) Inventors: Brian S. Modrzejewski, Keller, TX (US); Carlos Fenny, Arlington, TX (US)

(73) Assignee: Bell Helicopter Textron Inc., Fort Worth, TX (US)

(*) Notice: Subject to any disclaimer, the term of this patent is extended or adjusted under 35 U.S.C. 154(b) by 346 days.

(21) Appl. No.: 14/283,555

(22) Filed: May 21, 2014

(65) Prior Publication Data
US 2015/0341989 A1    Nov. 26, 2015

(51) Int. Cl.
*H05B 3/34* (2006.01)
*A61F 7/00* (2006.01)
*A61F 7/02* (2006.01)
*A41D 1/04* (2006.01)
*A41D 31/00* (2006.01)
*A41D 13/005* (2006.01)
*F41H 1/02* (2006.01)

(52) U.S. Cl.
CPC ............... *H05B 3/342* (2013.01); *A41D 1/04* (2013.01); *A41D 13/0051* (2013.01); *A41D 31/00* (2013.01); *A61F 7/007* (2013.01); *F41H 1/02* (2013.01); *A61F 2007/0071* (2013.01); *A61F 2007/0234* (2013.01)

(58) Field of Classification Search
None
See application file for complete search history.

(56) References Cited

U.S. PATENT DOCUMENTS

| | | | | | |
|---|---|---|---|---|---|
| 3,397,302 | A | * | 8/1968 | Hosford | B64D 15/12 219/202 |
| 5,148,002 | A | * | 9/1992 | Kuo | H01Q 1/273 219/211 |
| 5,545,194 | A | * | 8/1996 | Augustine | A61F 7/0097 219/212 |
| 5,561,173 | A | * | 10/1996 | Dry | A61L 27/48 428/320.2 |
| 5,800,480 | A | * | 9/1998 | Augustine | A61F 7/10 5/421 |
| 5,928,548 | A | * | 7/1999 | Johansson | A47C 7/748 219/217 |
| 6,582,456 | B1 | * | 6/2003 | Hand | A61F 7/007 219/212 |

(Continued)

OTHER PUBLICATIONS

Office Action dated Nov. 27, 2014 from counterpart EP App. No. 14175315.2.

(Continued)

*Primary Examiner* — Joseph M Pelham
(74) *Attorney, Agent, or Firm* — James E. Walton

(57) ABSTRACT

A heater system includes a bag forming a cavity, a fluid bladder carried within the cavity and forming a fluidly sealed chamber. The fluid bladder being configured to store electrorheological fluid within a fluidly sealed chamber. The heater system further including an electrical wire in fluid communication with the electrorheological fluid and a heater blanket carried within the cavity. The method includes altering the electrorheological fluid with a current and providing heat with a heater blanket.

18 Claims, 7 Drawing Sheets

(56) References Cited

U.S. PATENT DOCUMENTS

| | | | |
|---|---|---|---|
| 6,635,189 B2* | 10/2003 | Suh | C10M 171/001 |
| | | | 252/572 |
| 7,550,189 B1 | 6/2009 | McKnight | |
| 2006/0080756 A1 | 4/2006 | Goldfine | |
| 2006/0099808 A1 | 5/2006 | Kondo | |
| 2008/0306419 A1 | 12/2008 | Bishop | |
| 2015/0373781 A1* | 12/2015 | Augustine | H05B 1/0272 |
| | | | 219/212 |

OTHER PUBLICATIONS

Office Action dated Dec. 11, 2014 from counterpart EP App. No. 14175315.2.

* cited by examiner

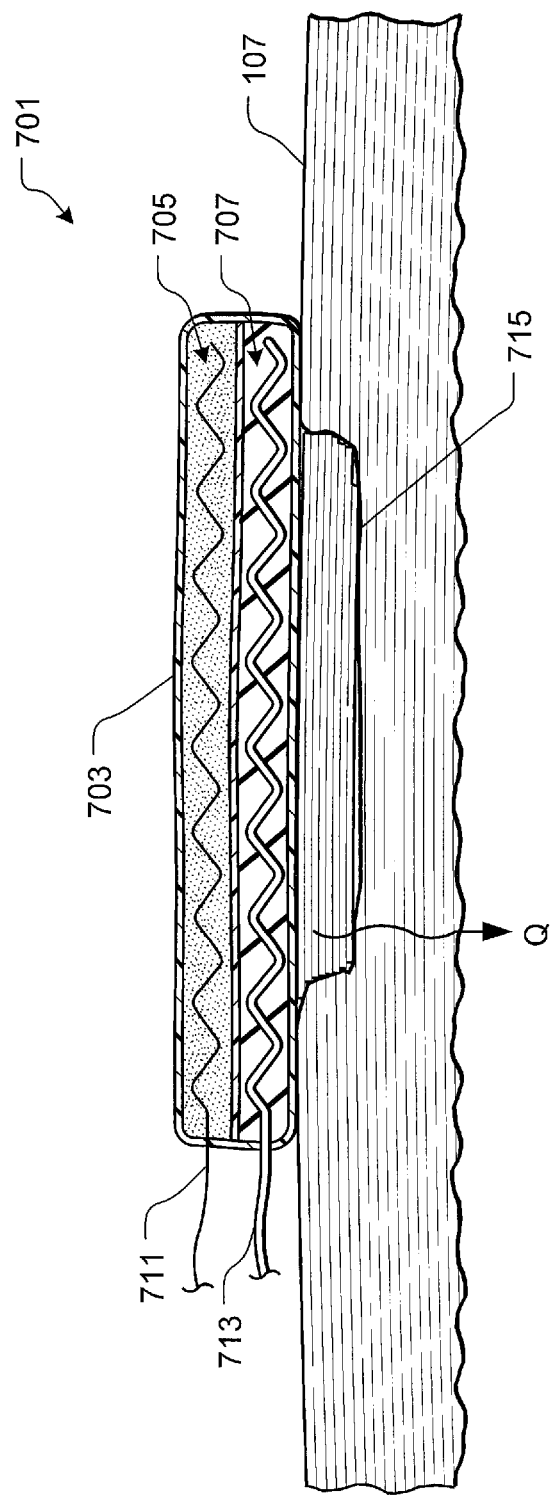

US 9,585,198 B2

VARIABLE STIFFNESS BLANKET WITH VARIABLE HEATING

BACKGROUND

1. Field of the Invention

The present application relates generally to heater blankets, more specifically, to a heater blanket having variable stiffness.

2. Description of Related Art

Heater blankets are well known in the art for providing warmth to an object. Conventional heater blankets typically include an electrical wire disposed within a thermal conductive body and when activated, the electrical energy traveling through the wire creates heat, which in turn warms the object that the heater blanket is place thereon.

In one application of use, a heater blanket is utilized in the aircraft industry during repair of a laminate structure. For example, a plurality of repair plies are stacked and placed on a damaged composite surface and thereafter cured with the heater blanket. The heat from the heater blanket causes the adhesive disposed within the plies to cure.

A common disadvantage with conventional heater blankets is the inability to retain the heater blanket in a fixed position on the plies without the use of straps and/or a vacuum bag. Further, conventional heater blankets are not always adapted to conform to the outer surface of the structure, thereby limiting use.

Although the foregoing developments in the field of heater blankets represent great strides, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 7 is a cross-sectional view of a heater blanket system in accordance with an alternative embodiment of the present application;

Figure 1:
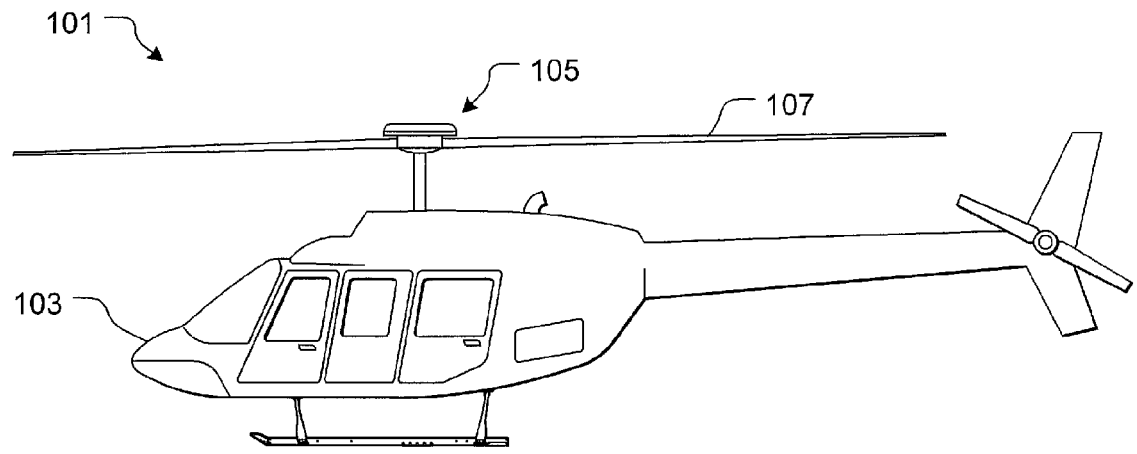
FIG. 1 is a side view of a helicopter in accordance with a preferred embodiment of the present application.

While the system and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the apparatus and method are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system of the present application overcomes the abovementioned problems commonly associated with conventional heater blankets. Specifically, the heater system of the present application includes one or more fluid bladders having electrorheological fluid disposed therein, and when energized with an electrical charge, changes fluid viscosity. This feature enables the fluid bladder to conform to the contouring of the object that the heater system is attached thereto. The system is also provided with a heater blanket secured to the fluid bladder and configured to exude heat to warm the object that the bag is attached thereto. Further detailed description of these features are provided below and illustrated in the accompanying drawings.

The system and method of the present application will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Referring now to the drawings wherein like reference characters identify corresponding or similar elements throughout the several views, FIG. 1 depicts an aircraft 101 in accordance with a preferred embodiment of the present application. In the exemplary embodiment, aircraft 101 is a helicopter having a fuselage 103 and a rotor system 105 carried thereon. A plurality of rotor blades 107 is operably associated with rotor system 105 for creating flight.

Figure 2:
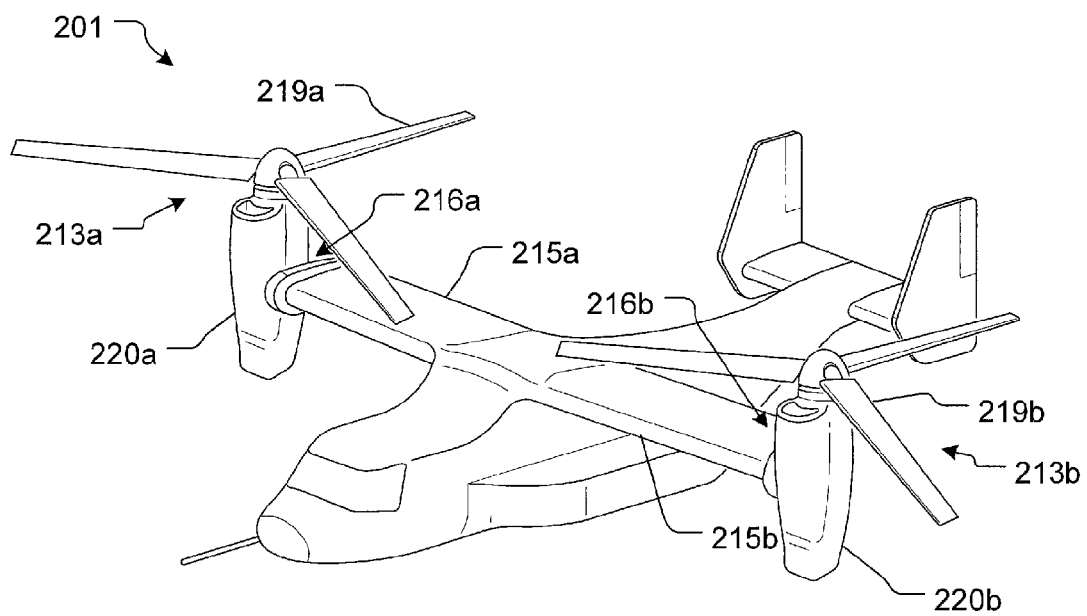
FIG. 2 is a perspective view of a tiltrotor aircraft according to an alternative embodiment of the present application.
Figure 3:
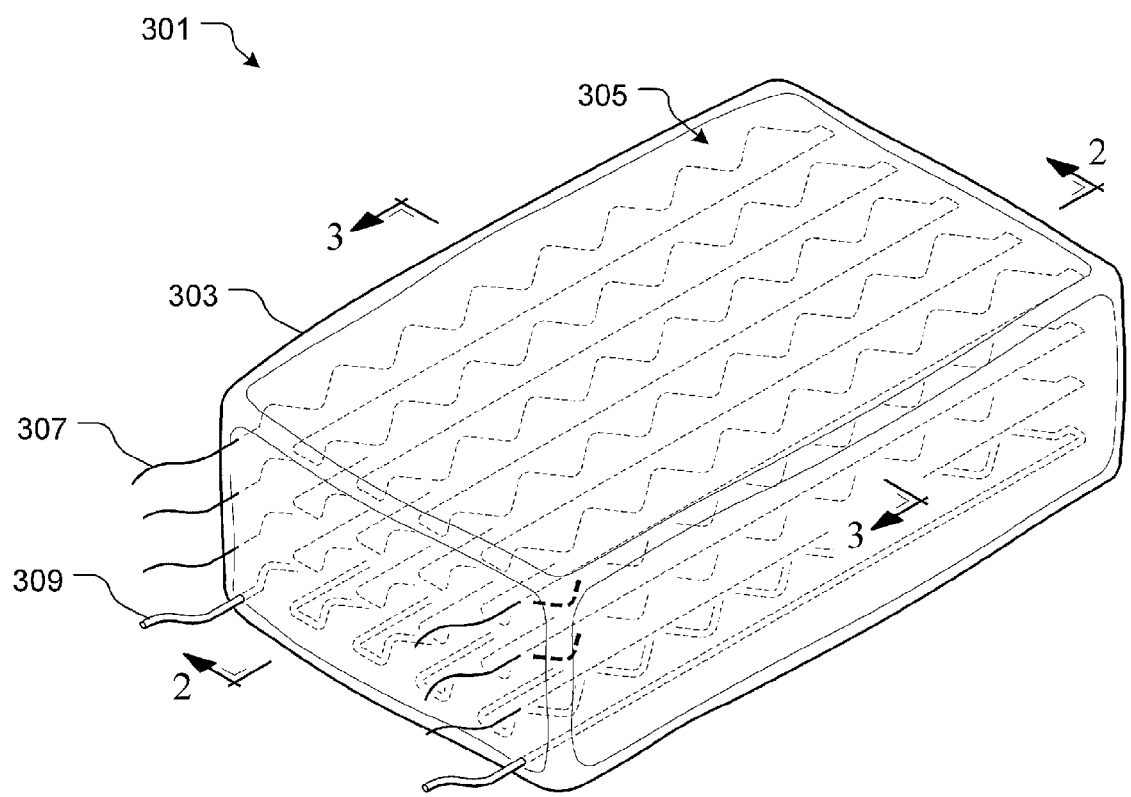
FIG. 3 is an oblique view of the heater blanket system in accordance with a preferred embodiment of the present application.
Figure 4:
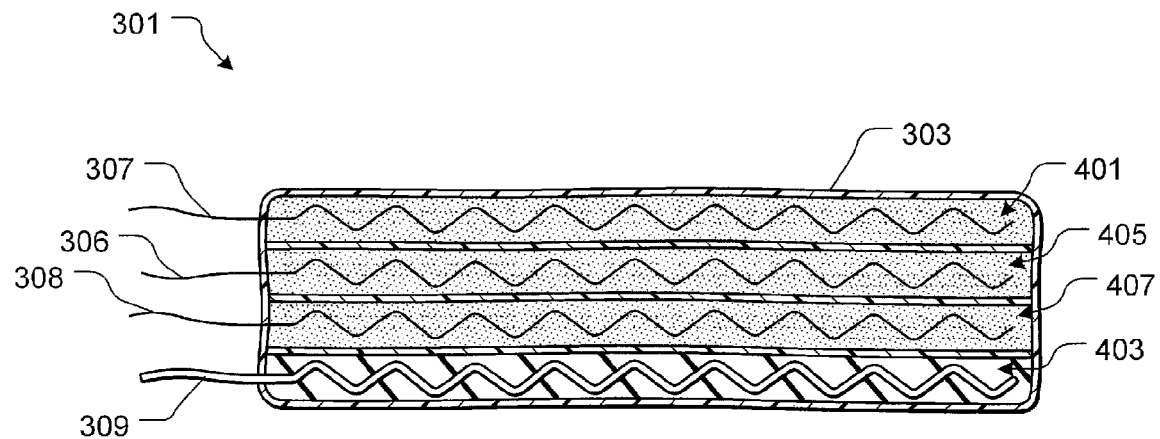
FIG. 4 is a cross-sectional view of the system of FIG. 3 taken at IV-IV.
Figure 5:
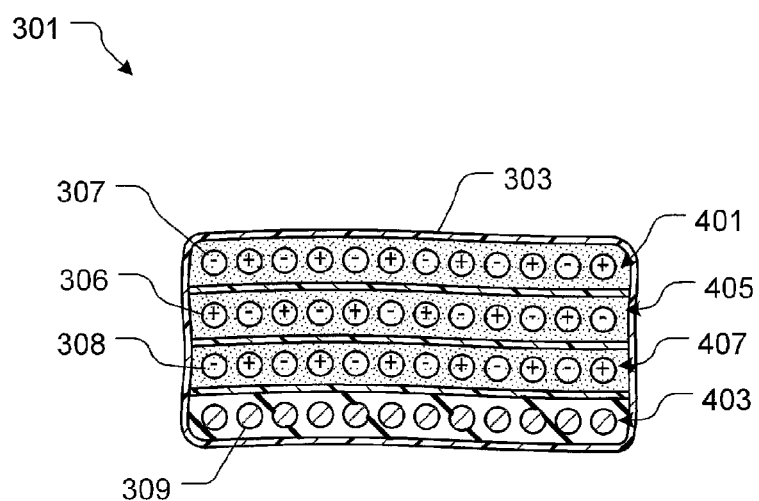
FIG. 5 is a cross-sectional view of the system of FIG. 3 taken at V-V.
Figure 6A:
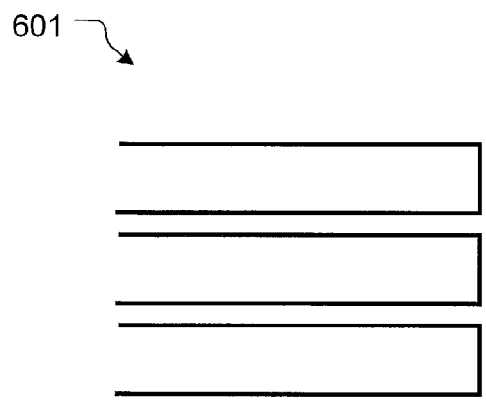
FIGS. 6A, 6B, 6C, and 6D are simplified wiring schematics of the electrical wire of the system of FIG. 3.
Figure 6B:
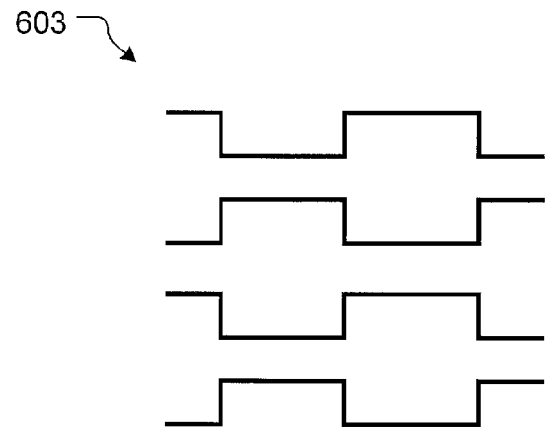
Figure 6C:
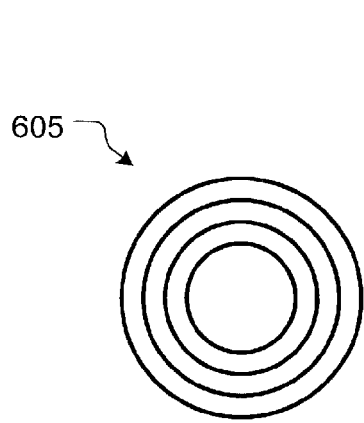
Figure 6D:
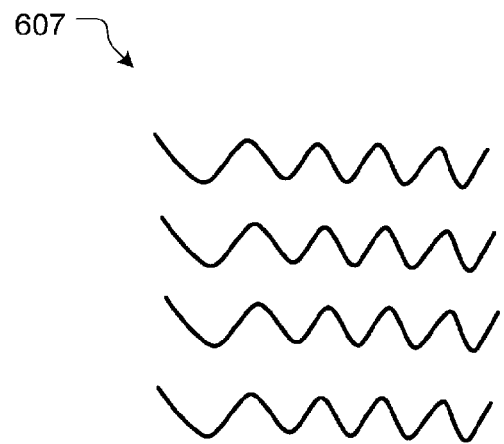

In the contemplated embodiment, heater system is operably associated with a helicopter. However, it will be appreciated that the system of the present application could also be utilized with different types of rotary aircraft, vehicles, clothing, medical devices, and the like in lieu of components of a helicopter. For example, FIG. 2 illustrates a tiltrotor aircraft 201 that utilizes the heater system in accordance with the present application.

Tiltrotor aircraft 201 includes rotor assemblies 213a and 213b that are carried by wings 215a and 215b, and are disposed at end portions 216a and 216b of wings 215a and 215b, respectively. Tilt rotor assemblies 213a and 213b include nacelles 220a and 220b, which carry the engines and transmissions of tilt rotor aircraft 201, as well as, rotor proprotors 219a and 219b on forward ends 221a and 221b of tilt rotor assemblies 213a and 213b, respectively. Tilt rotor assemblies 213a and 213b move or rotate relative to wing members 215a and 215b between a helicopter mode in which tilt rotor assemblies 213a and 213b are tilted upward, such that tilt rotor aircraft 201 flies like a conventional helicopter; and an airplane mode in which tilt rotor assemblies 213a and 213b are tilted forward, such that tilt rotor aircraft 201 flies like a conventional propeller driven aircraft.

Figures 8, 9:
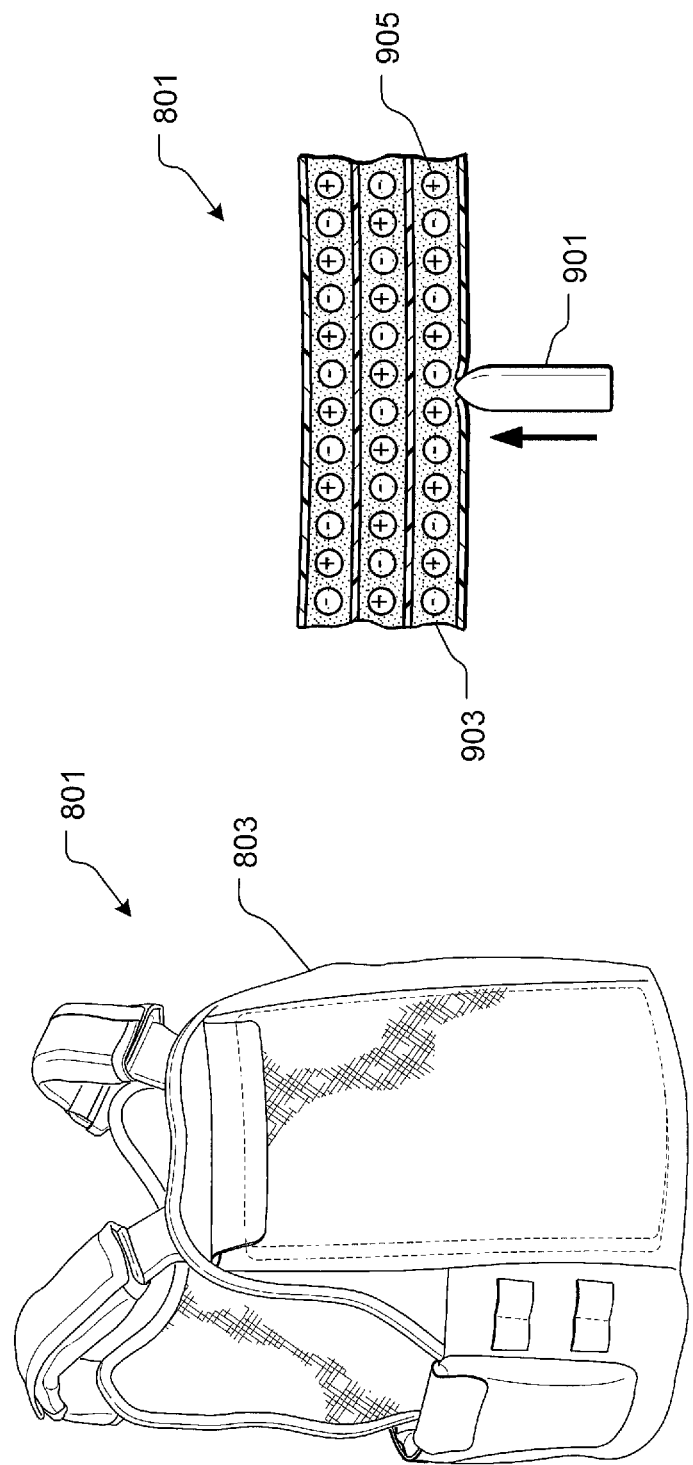
FIG. 8 is an oblique view of a heater blanket system in accordance with an alternative embodiment of the present application.
FIG. 9 is a partial cross-sectional view of the system of FIG. 8.

FIGS. 3-6 depict various views of a heater system 301 in accordance with a preferred embodiment of the present application. In the contemplated embodiment, system 301 is shown operably associated with a rotor blade 107, as depicted in FIG. 7. However, it will be appreciated that the features discussed herein could be utilized on different devices, for example, a body suit (see FIG. 8) or a medical device (see FIG. 10). These and other contemplated embodiments incorporate the features discussed herein.

In the preferred embodiment, system 301 includes one or more of a bag 303 that forms a fluidly sealed interior area 305 configured to carry therein one or more fluid bladders 401 and a heater blanket 403. In the exemplary embodiment, system 301 includes three fluid bladders 401, 405, 407 fluidly separated from each other. Disposed within each fluid chamber is an electrical wire 307 in fluid communication with the electrorheological fluid carried within the fluid bladders.

One of the unique features believed characteristic of the present application is the use of electrorheological fluid carried within the fluid bladders. It should be appreciated that as an electrical charge is introduced into the fluid disposed within the fluid bladders, the fluid characteristics change, for example, the viscosity is altered. This feature provides significant advantages, namely, the bag 303 is placed on a contoured surface and retains that general shape of the contoured surface by altering the stiffness of the fluid disposed within bladders 401, 405, and 407. Thus, bag 303 is capable of retaining a shape without the need of a strap and/or a vacuum bag.

In the exemplary embodiment, it is contemplated having fluidly separable fluid bladders to control the stiffness of each bladder. However, alternative embodiments could include a single fluid bladder in lieu of the preferred plurality of bladders. It will be appreciated that having multiple fluid bladders attached to each other allows selective controlling of the fluid characteristics in each chamber, individually. For example, a user could induce more electrical energy to fluid bladder 401 than for fluid bladder 407. This feature will increase the stiffness of fluid bladder 401 over the fluid bladder 407, thereby manipulating the stiffness of each bag individually for a desired overall stiffness of the bag, which in turn allows the bag to fit more snugly to the object being placed thereon.

In the contemplated embodiment, individual electrical wires 306, 307, and 308 pass through respective fluid bladders 405, 401, and 407 and could be electrically charged as individually. Thus, more electrical energy could pass through wire 307 than wire 308 to create greater stiffness in bag 401 than bag 407.

Another unique feature believed characteristic of the present application is the use of a heater blanket 403 attached to the one or more fluid bladders. The heater blanket is composed of thermal conductive material configured to warm the object that system 301 is placed thereon. To achieve this feature, an electrical wire 309 passes through the thermal conductive material of blanket 403 and is configured to create heat as an electrical current passes therethrough, which in turn warms the surface of the object placed thereon.

In FIGS. 6A-6D, various views of different wire patterns are shown. It is contemplated having the wires travel in straight lines, as depicted in pattern 601, in the preferred embodiment; however, other patterns are considered in alternative embodiments. For example, as depicted in pattern 603, the wires can have a chevron pattern or as depicted in patter 605, a circular pattern or as depicted in 607, a wave pattern. The particular pattern of use is a design choice depending on the desired application of use.

In FIG. 7, a cross-sectional view of heater system 701 is shown operably associated with a damaged rotor blade 107. It will be appreciated that system 701 is substantially similar in form and function to system 301 and incorporates the features discussed above, and vice-versa.

Like system 301, the heater system 701 includes a bag 703 configured to carry one or more fluid bladders 705 and a heater blanket 707. Wires 711, 713 provide electrical energy to respective fluid bladder 705 and heater blanket 707 during use.

As depicted, the bag 703 rests on a repair patch 715, and during use, the system 701 creates heat with heater blanket 707, which in turn heats repair patch 715, as depicted with an arrow. The fluid bladder 705 is configured to conform to the contouring of the blade 107 to create maximum surface contact between the heater blanket 707 and the repair patch 715.

It will be appreciated that the features of systems 301 and 701 could be utilized with a bullet proof vest 801. In the contemplated embodiment, vest 801 includes a bag 803 that carries one or more fluid bladders 903 therein. The fluid bladders have the electrorheological fluid and a wire disposed therein. During use, a projective 901 attempts to penetrate bag 801 but is stopped by fluid bladders 903 as an electrical charge is created therein via the wire 905. This feature is achieved by activating a power source (not shown) which provides electrical energy through the wires disposed within the fluid bladders 903, which in turn alters the viscosity and stiffness of the fluid disposed therein.

Figure 10:
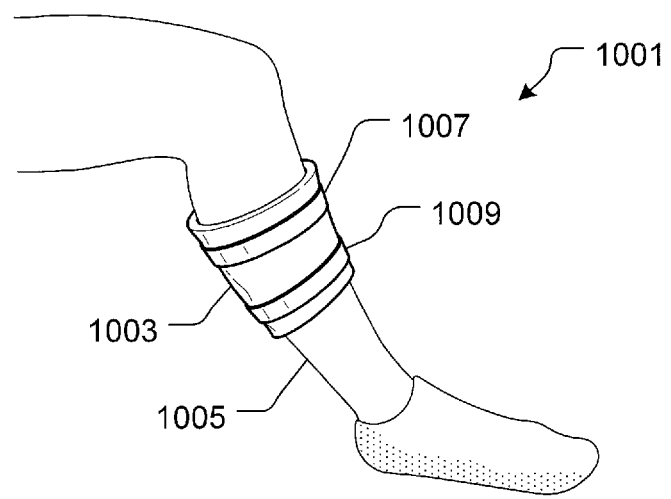
FIG. 10 is an oblique view of a heater blanket system in accordance with an alternative embodiment of the present application.

The features discussed herein could also be utilized with a medical device 1001, as depicted in FIG. 10. In the contemplated embodiment, medical device 1001 includes a bag 1003 substantially similar in form and function to one or more of the bags discussed above. Bag 1003 is secured to a leg 1005 of a patient via straps 1007, 1009 configured to wrap around the leg.

Figure 11:
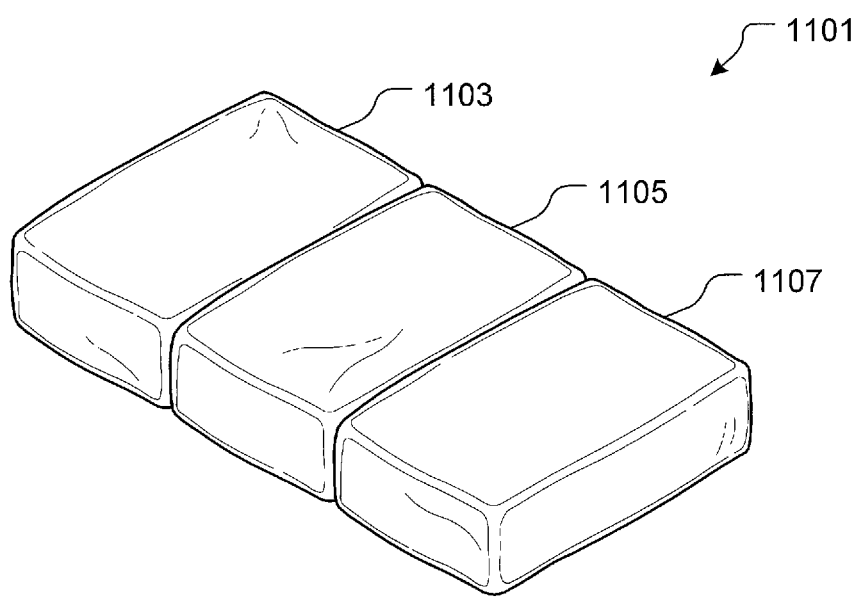
FIG. 11 is an oblique view of a heater blanket system in accordance with an alternative embodiment of the present application.

In FIG. 11, a system 1101 is shown having three bags 1103, 1105, and 1107 secured together and configured to provide selective fluid viscosity and heat for each bag, individually. Bags 1103, 1105, and 1107 share the same features as one or more of the bags discussed above. Thus, in the contemplated embodiment, system 1101 provide means to create variable heat and stiffness of multiple bags used together.

It will be appreciated the features discussed herein, specifically, the altering of the electrorheological fluid and/or the amount of heat applied to a structure via the heater blanket, is variable. Thus, it is contemplated having the necessary electrical devices (not shown) that vary the amount of electrical energy provided to the electrorheological fluid and the heater blanket to create a desired fluid stiffness and/or heat source.

It is apparent that a system and method with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A heater system, comprising:
a first bag forming a cavity;
a fluid bladder carried within the cavity and forming a fluidly sealed chamber, the fluid bladder being configured to store electrorheological fluid within a fluidly sealed chamber;
an electrical wire in fluid communication with the electrorheological fluid; and
a heater blanket carried within the cavity;
a second bag secure to and placed adjacent to the first bag;
wherein current passing through the electrical wire changes the fluid properties of the electrorheological fluid; and
wherein the heater system creates heat, which in turn warms an object that the heater system is placed thereon.

2. The system of claim 1, wherein the heater blanket is composed of thermal conductive material.

3. The system of claim 2, further comprising:
an electrical wire passing through thermal conductive material.

4. The system of claim 2, the heater system comprising:
an electrical wire configured to create heat to warm the object that the heater system is placed thereon.

5. The system of claim 1, further comprising:
a second fluid bladder carried within a second cavity of the second bag, the second fluid bladder being configured to form a fluidly sealed second chamber to store electrorheological fluid therein.

6. The system of claim 5, further comprising:
a second electrical wire in fluid communication with the electrorheological fluid of the second fluid bladder.

7. The system of claim 6, further comprising:
a second heater blanket carried within the second cavity.

8. A vest, comprising:
a first bag forming a cavity;
a fluid bladder carried within the cavity and forming a fluidly sealed chamber, the fluid bladder being configured to store electrorheological fluid within a fluidly sealed chamber; and
an electrical wire in fluid communication with the electrorheological fluid;
a second bag secure to and placed adjacent to the first bag
wherein current passing through the electrical wire changes the fluid properties of the electrorheological fluid.

9. The vest of claim 8, further comprising:
a heater blanket carried within the cavity of the bag;
wherein the heater blanket creates heat, which in turn warms a surface that the vest is secured to.

10. The system of claim 9, wherein the heater blanket composed of thermal conductive material.

11. The system of claim 10, further comprising:
an electrical wire passing through thermal conductive material.

12. The system of claim 9, the heater system comprising:
an electrical wire configured to create heat to warm the object that the heater system is placed thereon.

13. The system of claim 8, further comprising:
a second fluid bladder carried within a second cavity of the second bag, the second fluid bladder being configured to form a fluidly sealed second chamber to store electrorheological fluid therein.

14. The system of claim 13, further comprising:
a second electrical wire in fluid communication with the electrorheological fluid of the second fluid bladder.

15. The system of claim 14, further comprising:
a second heater blanket carried within the second cavity.

16. A method to heat a surface, comprising:
creating a fluidly sealed first chamber;
storing a electrorheological fluid within the fluidly sealed first chamber;
creating a fluidly sealed second chamber;
storing a electrorheological fluid within the fluidly sealed second chamber;
altering the electrorheological fluid with an electrical current in the second chamber and in the first chamber; and
heating the surface with a heater blanket secured to the fluidly sealed first chamber;
wherein a stiffness of the first chamber is selectively varied compared to a stiffness of the second chamber.

17. The method of claim 16, wherein the feature of heating the surface is achieved by an electrical wire.

18. The method of claim 16, wherein the feature of altering the electrorheological fluid is achieved by passing an electrical wire through the fluidly sealed first chamber.

* * * * *